US005656502A

United States Patent [19]

MacKay et al.

[11] Patent Number: 5,656,502

[45] Date of Patent: Aug. 12, 1997

[54] TEST STRIP HOLDER AND METHOD OF USE

[75] Inventors: Dana H. MacKay; Robert A. Fredrickson, both of Prince Edward Island, Canada

[73] Assignee: Diagnostic Chemicals Limited, Charlottetown, Canada

[21] Appl. No.: 476,036

[22] Filed: Jun. 7, 1995

[51] Int. Cl.[6] .................... G01N 33/48

[52] U.S. Cl. .................... 436/180; 436/164; 422/58; 422/61

[58] Field of Search .................... 422/56–58, 61; 436/169, 180

[56] References Cited

U.S. PATENT DOCUMENTS 3,884,641 5/1975 Kraffczyk et al. .
4,066,646 1/1978 LeBlanc, Jr. et al. .
4,323,536 4/1982 Columbus .................... 422/56
4,624,929 11/1986 Ullman .
4,774,192 9/1988 Terminiello et al. .
4,857,453 8/1989 Ullman et al. .
4,877,580 10/1989 Aronowitz et al. .................... 422/58
4,980,298 12/1990 Blake et al. .
4,999,285 3/1991 Stiso .................... 435/7.9
5,135,873 8/1992 Patel et al. .................... 436/180
5,145,789 9/1992 Corti et al. .
5,207,984 5/1993 Kheiri .................... 422/58
5,256,372 10/1993 Brooks et al. .
5,356,782 10/1994 Moorman et al. .................... 435/7.9
5,366,902 11/1994 Cox et al. .................... 422/58
5,384,264 1/1995 Chen et al. .................... 436/525
5,500,375 3/1996 Lee-Own et al. .................... 436/514
5,504,013 4/1996 Senior .................... 422/58

FOREIGN PATENT DOCUMENTS

0560411A2 9/1993 European Pat. Off. .
WO9402850 2/1994 WIPO .

*Primary Examiner*—Lyle A. Alexander
*Attorney, Agent, or Firm*—Oliff & Berridge

[57] ABSTRACT

A test strip holder includes an elongated hollow member having an open end and a closed end. A support is provided that positions a test strip within the elongated hollow member spaced from inner walls of the elongated hollow member. At least one vent is positioned between the open end and the closed end of the elongated hollow member. The distance from the open end to the at least one vent opening defines the maximum height of liquid able to enter the elongated hollow member from the open end other than by capillary action. The elongated member may be formed as a tubular conduit. Alternatively, the elongated member may include a test strip receiving part and a test strip covering part, wherein the test strip receiving part may or may not be hingedly connected to the test strip covering part.

24 Claims, 7 Drawing Sheets 2
3
4
5
6
9
10
33
34
A
C
L
L1

TEST STRIP HOLDER AND METHOD OF USE

BACKGROUND

This invention relates to a holder for a test strip and a method of using the holder. The test strip holder positions a test strip within a liquid to ensure that liquid contacts and moves up the test strip only by capillary action.

Conventional test strips are hand-held and immersed in the liquid. The test strip is then removed from the liquid and the results are determined from reading the test strip. In this "immersion" method, the tester is required to physically hold the test strip in the liquid. This can result in problems arising from contamination of the test strip from the tester's fingers, which may result in unreliable or tainted results.

Further problems may arise from prolonged contact of the test strip with the liquid to be tested. Some test strips require contact with a liquid for a predetermined time period. If the strip contacts the liquid for an extended period of time, the results may be faulty or unreliable.

Other known test strips require application of a specific volume to the test strip, for example a predetermined number of drops. Other test strips require immersion of the test strip in a liquid up to a prescribed height for a designated period of time. These types of test strips require extensive and exacting tester interface. The tester must maintain constant surveillance of the test strip and liquid to ensure proper test conditions. This is an inefficient use of the tester's time. Further, it can easily lead to errors in the testing.

Holders for test strips are known that include a test strip enclosed within a housing. However, this type of test strip holder also suffers from the above disadvantages, such as the need for continuous monitoring and careful measuring. The housing must be dipped into a liquid to a certain height for a predetermined time. The tester must hold the holder or cause the holder to be supported at the predetermined depth for the designated time period. If the test strip and housing are inserted beyond the depth and/or for more or less than the predetermined time, the results from the test may be inaccurate and unreliable.

Further, known test strip holder devices do not include any structure to assure that the liquid contacts the test strip only up to a certain predetermined height. Even if the housing is provided with a mark designating the insertion depth, the tester must manually hold the test strip holder in the liquid for a designated period of time. Further, depending on the clarity of the liquid and the container in which the liquid is held, it is difficult to accurately position the test strip holder with the mark positioned at the surface of the liquid.

Known test strip holders also do not ensure the positioning of the test strip away from the internal side walls of the holder. Therefore, the liquid may travel up the side walls of the test strip holder by capillary action and prematurely contact the test strip, rather than only travel up the test strip. Premature contact of the test strip with liquid may cause faulty and unreliable test results, especially if the test strip is provided with a plurality of test strip zones that are to be sequentially contacted. Moreover, direct and prolonged liquid contact with the strip may cause unreliable test results.

SUMMARY OF THE INVENTION

The invention provides a reliable test strip holder and method of use of the test strip holder. The test strip holder can be inserted into any depth in a liquid to be tested and left in the liquid with testing zones of the test strip out of direct contact with the liquid. The tester is not required to continuously monitor the insertion depth of the test strip. The test strip holder maintains the test strip spaced from the sides of the test strip holder, wherein the liquid flows up the test strip by capillary action within the strip only. The test strip is not wetted by liquid on the inner walls of the elongated hollow member. This avoids premature contact of the test strip with the liquid and unreliable testing results.

The invention provides a test strip holder and method of use that overcomes the problems associated with known test strip holders and methods. The test strip holder accurately positions a test strip in a liquid so liquid travels up the test strip only by capillary action of the strip and liquid.

The invention provides a test strip holder including an elongated hollow member that is open at one end and sealingly and air-tightly closed at the other end. The elongated hollow member includes support structure for positioning a test strip away from the side walls of the elongated hollow member. The elongated hollow member also includes at least one vent positioned at a predetermined location between the open and closed ends, preferably proximate the open end of the elongated hollow member.

When the test strip holder is inserted into a liquid, the liquid rises inside the elongated hollow member only to the level of the at least one vent. Air or other ambient atmosphere in the interior of the elongated hollow member can initially exit through the at least one vent as the liquid enters. Once the liquid covers the at least one vent, the pressure of the air or ambient atmosphere in the elongated hollow member above the at least one vent prevents the liquid from further entering the elongated hollow member. Thus, the test strip is in contact with the liquid only in a predetermined designated area, designed for direct contact with the liquid. The position of the vent on the sidewall of the elongated hollow member determines the maximum height that the liquid can actually enter the elongated hollow member. The actual test strip test zones are preferably not in direct contact with the liquid and are wetted only by capillary action of the liquid on the test strip.

BRIEF DESCRIPTION OF THE DRAWINGS

Embodiments of the invention will be described in detail with reference to the following drawings in which like reference numerals refer to like elements and wherein.

DESCRIPTION OF PREFERRED EMBODIMENTS

Figure 1:
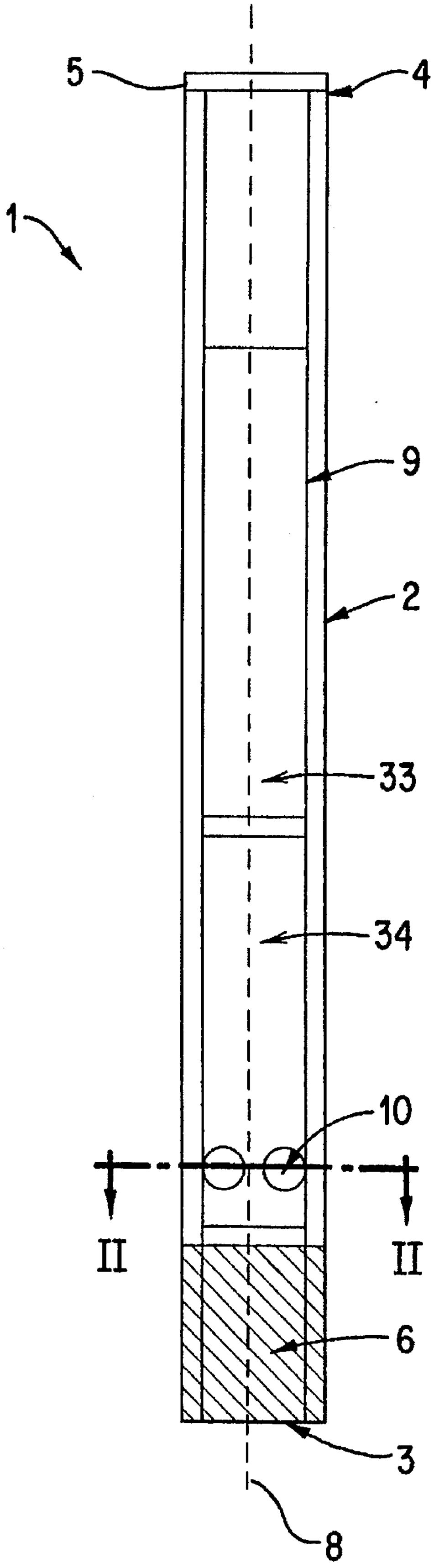
FIG. 1 is a sectional view of a test strip holder according to a first embodiment of the invention.

The elongated hollow member of the holder may be formed with a rounded cross-section, for example, as a tubular conduit. Alternatively, the elongated hollow member may be formed as two separate mateable parts, which are sealed around their periphery. The elongated hollow member may be formed in other configurations, as long as the elongated hollow member defines an open end and a sealed closed end with at least one vent positioned between the open and closed ends. The position of the at least one vent in the elongated hollow member can be varied to vary the depth of immersion of the test strip.

The elongated hollow member also defines support structure for the test strip, which maintains the test strip spaced from the walls of the elongated hollow member. The support structure may be an element separate from the elongated hollow member and inserted into the elongated hollow member. Alternatively, the support structure may be formed integrally with the elongated hollow member.

The support structure may take any form appropriate complementary to the test strip holder, as long as the test strip is maintained spaced from the walls of the elongated hollow member. This prevents the test strip zones from being contacted by any liquid on the sidewalls of the elongated hollow member. Liquid normally flows by capillary action in a path of "least resistance." Contact between the test strip and the sidewalls of the test strip holder creates a low resistance capillary channel and provides a "short circuit" for the liquid up the edges of the test strip thereby bypassing a front surface of the test strip. This can lead to erroneous and unreliable results.

The spacing of the test strip from the side walls of the elongated hollow member ensures that liquid, under normal atmospheric conditions, flows up the test strip by capillary action when the test strip holder is inserted open end down into a liquid. Liquid does not contact the test strip from the side walls of the test strip holder based on the configuration of the test strip holder. The size of the test strip holder and the configuration of the open end may vary depending on characteristics of the liquid to be tested, but can be readily determined by routine experimentation.

The closed end of the elongated hollow member is sealed so that air cannot exit. The absence of air exiting prevents liquid from moving up the elongated hollow member beyond the at least one vent other than by capillary action within the test strip. The position of the at least one vent in the elongated hollow member can be predetermined to select the depth of immersion of the test strip.

The test strip can take any appropriate form and can include at least two separate and distinct testing zones. These testing zones are designed to bind moving liquid reagents to the test strip in proportion to the concentration of the substance tested for in the liquid. The testing zones can measure for different substances within the liquid, thereby avoiding multiple tests and potential contamination of the liquid by different test strips and/or test strip holders. Therefore, it is important that the test strip be wetted by the capillary action of the liquid. Direct contact of liquid with the testing zones can alter the results or cause the test to be unreliable.

Further, the test strip may include a sample pad, conjugate pad, a membrane, which includes the testing zones used in the actual testing, and a wicking pad. A piece of opaque (e.g., white) waterproof tape may be applied over the sample and conjugate pads and a part of the membrane. The tape masks the strip during development and also eliminates confusion regarding the location of the zones during testing. The tape applies pressure to the sample pad to facilitate the liquid's flow on the test strip. Further, the tape protects the test strip during manufacturing and particularly during insertion into the test strip holder.

FIG. 1 illustrates a first embodiment of the test strip holder 1. The test strip holder 1 includes an elongated hollow member 2. Elongated hollow member 2 is preferably constructed from a clear transparent material. The elongated member 2 may be perfectly clear or opaque in all regions, except where testing zones of the test strip 9 (discussed hereinafter) are located. In that region, the elongated hollow member is preferably transparent to permit the test strip to be viewed. The elongated hollow member 2 may also be provided with indicia, such as graduations, markings or the like, for identifying the testing zones. The elongated hollow member 2 may be made from any suitable non-reactive material, such as plastic, glass, or other such materials.

Figure 2:
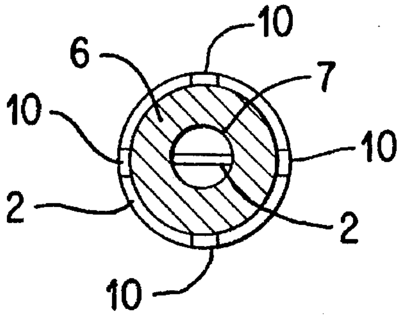
FIG. 2 is a cross-sectional view along line II—II of FIG. 1.

The elongated hollow member 2 has a circular cross-section, as seen in FIG. 2. However, any appropriate configuration of the elongated hollow member may be possible. The elongated hollow member 2 includes an open end 3 and an end 4 closed in an air-tight fashion.

Figure 1A:
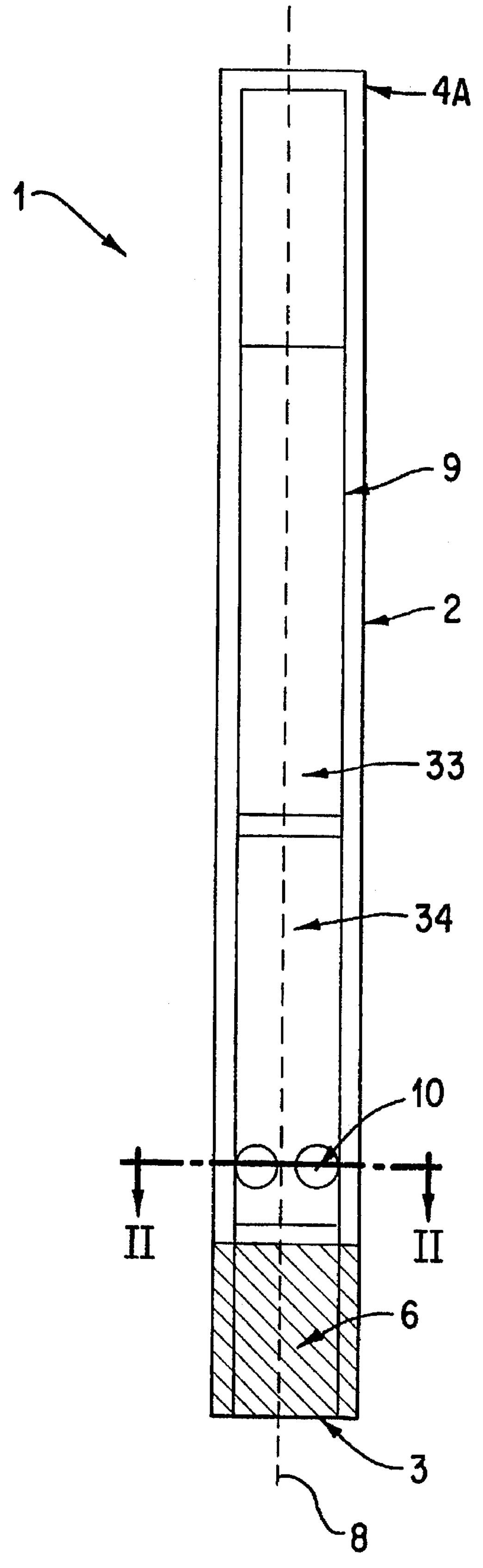
FIG. 1A is a sectional view of a test strip holder with a self sealed closed end according to a first embodiment of the invention.

The closed end 4 of the elongated hollow member may be formed in any suitable manner, as long as an airtight sealed end is formed. As seen in FIG. 1A, the closed end 4A may be formed by forming a sealed end from the elongated hollow member itself. Thus, the closed end 4A is sealed airtight to prevent the escape of air from the closed end 4A, without the need for additional components.

Alternatively, the closed end 4 may be sealed by an airtight sealing plug 5 inserted into the elongated hollow member 2 as in FIG. 1. Air tight sealing plug 5 prohibits air from entering or exiting the elongated hollow member 2 at the closed end 4. The airtight sealing plug 5 may rely on resilient characteristics to form the seal. Moreover, an adhesive (not shown) may be placed between the airtight plug 5 and the elongated hollow member 2 at the closed end 4 to enhance the seal at the closed end 4. Further, the seal at the closed end 4 may be enhanced by covering the plug 5 with suitable covering (not shown), including epoxy, wax, adhesive, or the like, or a further sealing cap.

The open end 3 of the elongated hollow member 2 includes an open plug 6, which may be made of rubber or other material. The open plug 6 is preferably fit within the open end of the elongated hollow member 2. The open plug 6 includes a through passage 7 co-linear with a longitudinal axis 8 of the elongated hollow member 2. The through passage 7 permits liquid to pass up through the open end 3 of the elongated hollow member 2 when the elongated hollow member 2 is inserted into a liquid, as described hereinafter.

The test strip 9 has a length substantially equivalent to the overall length of the elongated hollow member 2. The width of the test strip 9 is less than the inner diameter of the elongated hollow member 2. The width of the test strip 9 is substantially equal to the diameter of the through passage 7. Therefore, as seen in FIG. 1, when the test strip 9 is positioned within the elongated hollow member 2 and the through hole 7 of the open plug 6, the test strip 9 is held in the test strip holder 1 by a friction fit of the test strip 9 in the through passage 7. Further, the friction fit holds the test strip 9 spaced from the inner walls of the elongated hollow member 2.

The elongated hollow member 2 includes at least one vent or opening 10. The vents 10 may be circular, elliptical or any other appropriate shape. As seen in FIG. 1, there may be two or more vents 10. The vents 10 are preferably located proximate the open end 3 of the test strip holder 1. However the positioning of the vents 10 may be anywhere intermediate the open end 3 and closed end 4 of the elongated hollow member 2. As the vents 10 define the extent of liquid entry into the elongated hollow member 2 (as described hereinafter), it is preferable that the vents be located proximate the open end 3. Further, it is desirable to only physically and directly wet a designated area of the test strip 9, the vents should be positioned on the elongated hollow member 2 at a level approximately corresponding to the maximum level of direct physical wetting for the test strip 9.

The operation of the test strip holder will now be discussed, with reference to FIGS. 3A–3C. Initially, the test strip holder 1 is inserted into a container C holding the liquid L to be tested. Upon initial contact of the test strip holder 1 with the liquid L, the liquid L enters the open end 3 of the elongated hollow member 2 through the through passage 7 in the open rubber plug 6. Air within the elongated hollow member 2 is displaced up and exits the interior of the elongated hollow member 2 through the vents 10, as indicated by vent path A.

Figures 3A, 3B, 3C:
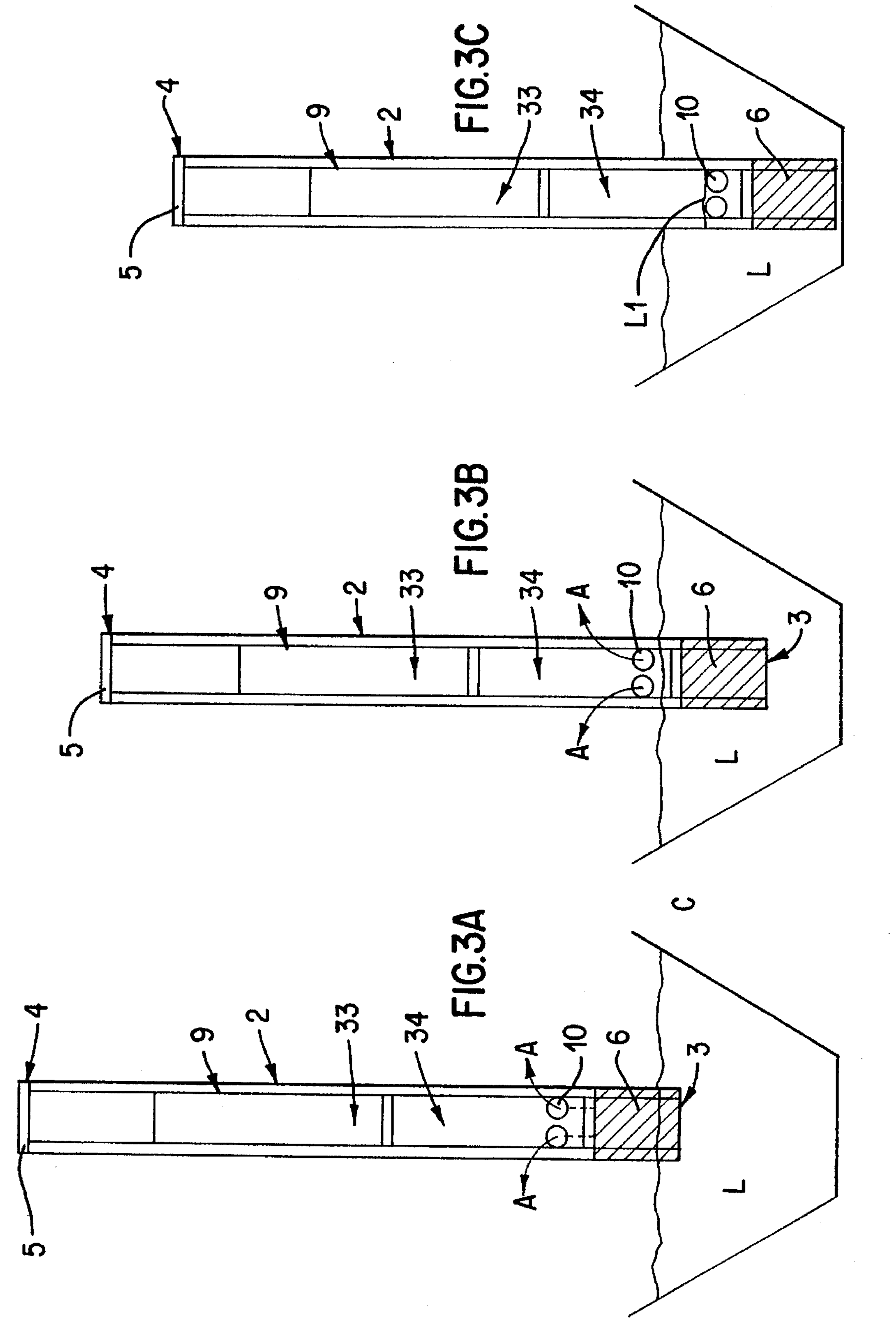
FIGS. 3A–3C illustrate the insertion of the test strip holder of FIG. 1 into a liquid to be tested.
Figure 4:
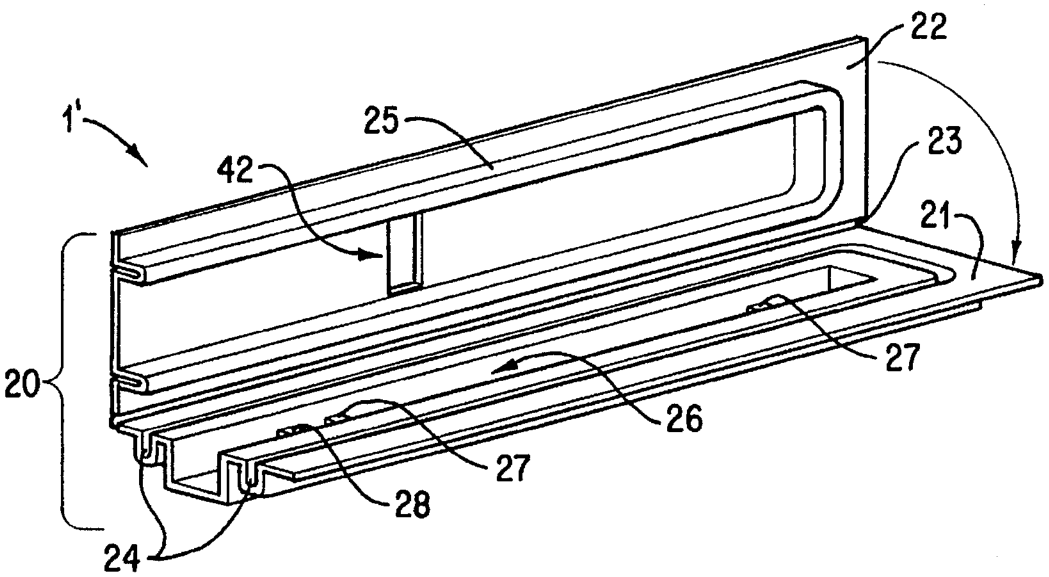
FIG. 4 is a front view of the test strip holder in the open condition according to a second embodiment of the invention.

Upon further insertion of the test strip holder 1 into the liquid L, the liquid L rises within the elongated hollow member 2, as in FIG. 3B. When the elongated hollow member 2 is immersed in the liquid L up to and covering the vents 10, as in FIG. 3C, the vent path A is closed as it is covered with liquid L. Therefore, the pressure within the elongated hollow member 2 above the liquid L increases. Liquid is prevented from further entering the elongated hollow member 2. The position of the vent 10 on the sidewall of the elongated hollow member 2 determines the maximum height that the liquid can actually enter the elongated hollow member 2.

The test strip 9 is positioned within the through passage 7 of the open rubber plug 6, thus spacing the test strip 9 from the walls of the elongated hollow member 2. Due to the spacing of the test strip 9 from the walls of the elongated hollow member 2, the capillary action of the liquid L contacting the test strip 9 is the only way that the liquid L contacts the testing zones Z1, Z2. The liquid L contacts only a bottom portion of the test strip 9 up to the level L1 defined by the vents 10 and does not directly contact the testing zones Z1 and Z2. Thus, erroneous and unreliable results, caused by direct contact of the liquid L and the zones Z1, Z2 of the test strip 9, are avoided.

A second embodiment of the test strip holder 1', is shown in FIGS. 4–8C. Here, an elongated hollow member 20 is formed by a test strip receiving part 21, which positions the test strip, and a test strip covering part 22. The test strip receiving part 21 and the test strip covering part 22 are connected at hinge 23. The parts 21, 22 are hinged together so the test strip covering part 22 closes onto the strip receiving part 21 to define the elongated hollow member 20. While the hinge 23 is shown parallel to a longitudinal axis of the parts 21, 22, the hinge could be provided parallel to an axis transverse to the parts 21, 22.

In the embodiments of FIGS. 4–8C, the test strip receiving part 21 includes a peripheral groove or channel 24, which is spaced from a test strip receiving channel 26. The test strip covering part 22 includes a peripheral protrusion 25 that is formed in a shape and size complementary to the peripheral groove or channel 24. When the test strip covering part 22 is pivoted about the hinge 23 and closed on the test strip receiving part 21, the peripheral protrusion 25 enters into and forms a seal with the peripheral groove or channel 24. The shape of the peripheral groove or channel 24 and the extending peripheral protrusion 25 mate so an airtight seal is formed around the elongated hollow member 20. The peripheral groove or channel 24 and peripheral extending protrusion 25 can mate in a "snapping" fashion to define the seal.

Further, an adhesive sealant (not shown) may be positioned within the groove or channel 24 prior to closing the test strip covering part 22 to enhance the airtight seal. Alternatively, a pressure sensitive adhesive (not shown) may be positioned within the peripheral groove or channel 24 or on the peripheral protrusion 25 so when the test strip covering part 22 is closed, the pressure sensitive adhesive is activated and the airtight sealing relation is enhanced.

Also, the test strip covering part 22 and the test strip receiving part 21 may be sealed by ultrasonic welding, rf (radio frequency) welding, plasma welding or the like. The welding may occur at the protrusion 25 and groove 24. Alternatively, the elongated hollow member 20 may be sealed by welding, not at the groove 24 or protrusion 25.

The peripheral groove or channel 24 and the peripheral protrusion 25 may be constructed in any shape and form, so long as the mating of the test strip receiving part 21 and test strip covering part 22 can form a sealed elongated hollow member 20.

The test strip receiving part 21 is shown in FIGS. 4–7 with the peripheral groove or channel 24 and the test strip covering part 22 having the peripheral protrusion 25. Alternatively, the test strip receiving part 21 may be provided with the protrusion 25 and the test strip covering part 22 may be provided with the peripheral groove on channel 24.

Figure 5:
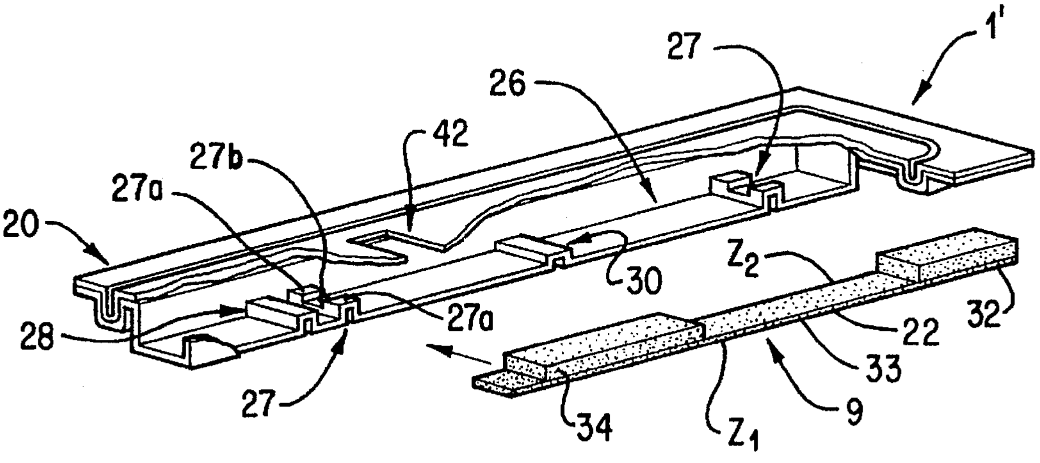
FIG. 5 is a part sectional view of the test strip holder of FIG. 4.
Figure 6:
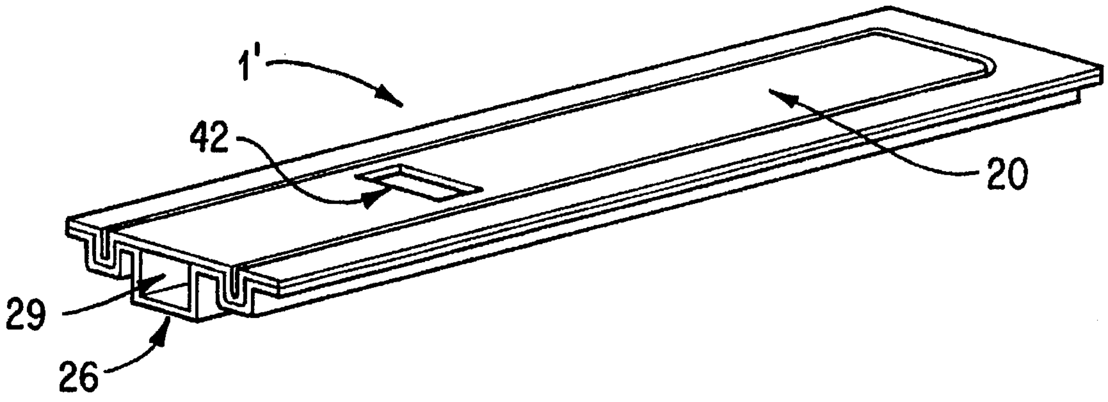
FIG. 6 is a front view of the test strip holder in a closed condition of FIG. 4.
Figure 7:
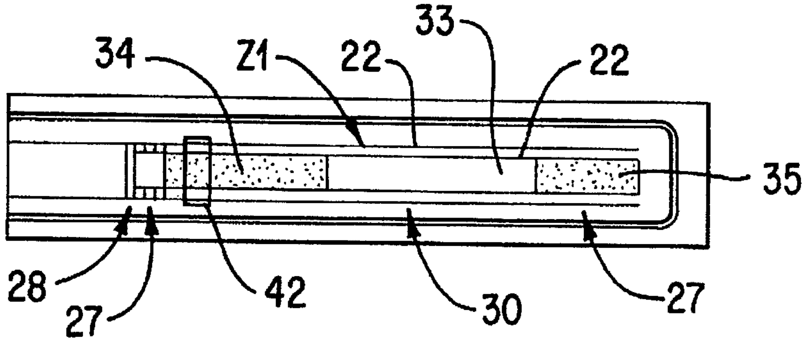
FIG. 7 is a cut away top sectional view of the test strip holder of FIG. 4.

The test strip channel 26 in the test strip receiving part 21 preferably includes at least two notched test strip holders 27. The notched test strip holders 27 may be integral with the elongated holder member 20 or be a separately attached element. The notched test strip holders 27 include two raised side portions 27*a* surrounding a planar center support surface 27*b*. The test strip 9 is positioned on the planar center support surface 27*b*. Movement of the test strip 9 is constrained by the raised side portions 27*a*. As seen in FIG. 5, there are two notched test strip holders 27 to position the remote ends of the test strip 9 spaced from the walls of the elongated hollow member 20. While the figures show two notched strip holders, any number of notched strip holders may be used, as long as the test strip 9 is maintained spaced from the sidewalls.

A test strip stop 28 is positioned proximate the open end 29 of the elongated hollow member 20. The test strip stop 28 maintains the test strip 9 within the test strip channel 26, especially when the test strip holder 1' is vertical. The test strip stop 28 prevents the test strip 9 from slipping out of the test strip channel 26 and assists in permitting the bottom of the test strip 9 to be in contact with the liquid L.

A bottom support 30 can be provided within the test strip channel 26 for further supporting the test strip 9 from the inner walls of the elongated hollow member 20. While the figures show one bottom support 30, any number of bottom supports may be provided in the test strip channel 26.

The test strip covering part 22 includes a window or vent 42. The vent 42 is shown as an elongated rectangle having substantially the same width as the test strip channel 26. However, the vent 42 may take any appropriate size and shape as long as the air can be vented from the test strip channel 26. The vent 42 functions substantially similar to the vents 10 of the first embodiment.

A test strip 9 shown in FIG. 5, can be used with either embodiment. The test strip 9 includes at least two separate and distinct test strip zones Z1, Z2 at membrane 33. These zones Z1, Z2 can bind the moving liquid reagents to the test strip 9 in proportion to the concentration of the substance tested for in the liquid L. The zones Z1, Z2 can measure for different substances within the liquid, therefore, it is important that the test strip be appropriately contacted by the capillary action of the liquid L. Direct contact of liquid L with the zones Z1, Z2 can alter the results or cause the test to be ruined.

Further, the test strip may include a sample pad 34, and conjugate pad under the sample pad and a wicking pad 35 contacting the membrane 33. A piece of white opaque waterproof tape (not shown) may be applied over the sample pad 34 and a part of the membrane 33. The opaque waterproof tape masks the test strip 9 during development. The tape also eliminates confusion regarding the location of the zones Z1, Z2 during testing. The tape applies pressure to the sample pad 34 and to the underlying conjugate pad to facilitate the liquid's flow up the test strip 9. The tape protects the test strip 9 during manufacturing and during insertion of the test strip 9 into the test strip holder 1, 1' or 1".

Test strip zones Z1, Z2 determine the presence of certain substances. The number of test strip zones is not limited to two, and any number of test strip zones Z1, Z2 may be provided. Further, any test strip 9 may be used with the test strip holders 1, 1' or 1". The type of test strip 9 may be changed, as needed, for the specified compound that the test is designed to discover.

Suitable test strips 9 include strips of material impregnated with compounds, which react with other compounds, normally in a liquid. The reaction may, for example, cause a change in color of the impregnated strip, where the change in color is representative of the concentration of the compounds in the liquid. Examples of such strips are pH strips; pregnancy test strips; immunoassay test strips; antigen, antibody and polynucleotide test strips; and test strips of analytes, such as drugs, metabolites, pesticides, pollutants and the like. The above types of test strips are only examples and any other suitable test strip may be used in the test strip holder 1, 1' or 1". A detailed discussion of examples of suitable test strips appears in U.S. Pat. No. 4,857,453, the entire contents of which are hereby incorporated by reference.

Figure 8C:
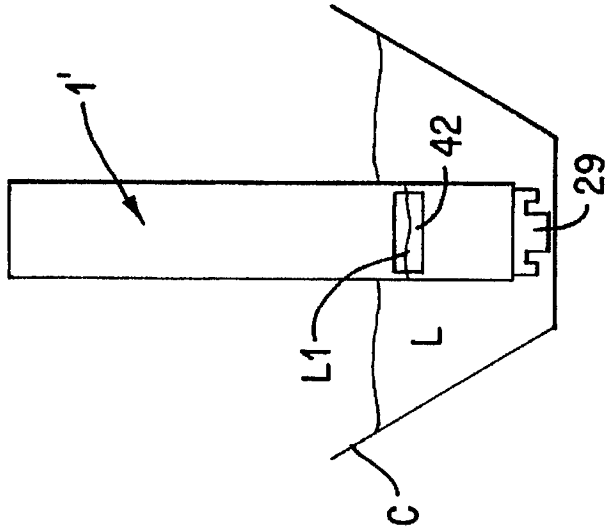
FIGS. 8A–8C illustrate the insertion of the test strip holder of FIG. 4 into a liquid.
Figure 8B:
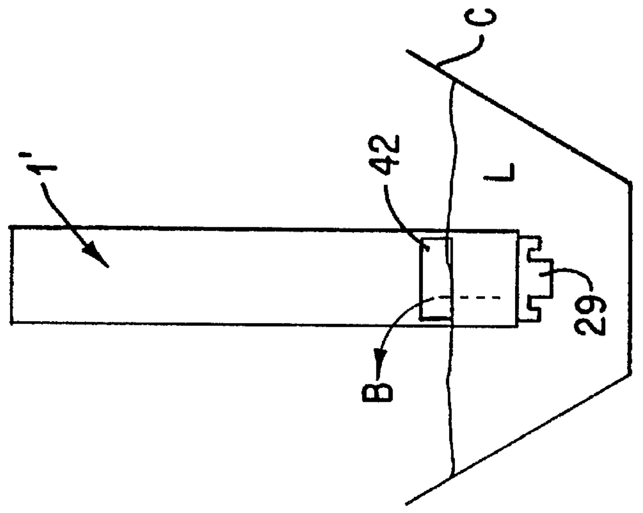
Figure 8A:
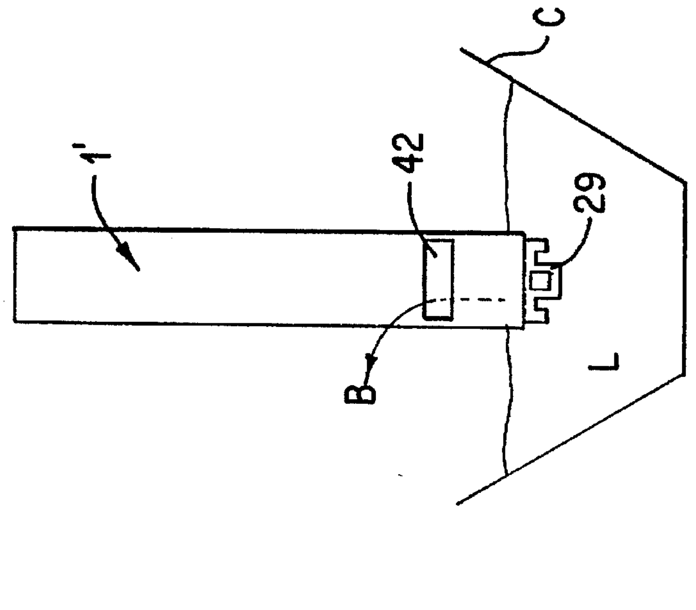

FIGS. 8A–8C show the immersion of the test strip holder 1' into a liquid L in a container C. Upon initial contact of the test strip holder 1' with the liquid L, the liquid L enters the open end 29 of the elongated hollow member 20. The air within the elongated hollow member 20 is displaced through the vent 42, as indicated by vent path B. Upon further insertion of the test strip holder 1' into the liquid L, the liquid L rises within the elongated hollow member 20. When the elongated hollow member 20 is immersed in the liquid L up to level L1 and covering the vent 42, the vent path B is no longer open to air. Therefore, the pressure within the remainder portion of the elongated hollow member 20 increases. Liquid L is thereby prevented from further entering the elongated hollow member 20.

The test strip 9 is in contact with the liquid L only in a predetermined designated area, designed for direct contact with the liquid. The position of the vent 42, on the sidewall of the elongated hollow member 20 determines the maximum height that the liquid L can actually enter the elongated hollow member 20. The actual test strip test zones Z1,Z2 are preferably not in direct contact with the liquid L and are wetted only by capillary action of the liquid on the test strip 9.

The test strip 9 is positioned within the test strip channel 26 and is spaced from the walls of the elongated hollow member 20 by the notched test strip holders 27 and the bottom support 30. The capillary action of the liquid L contacting the test strip 9 permits the liquid to contact the testing zones Z1,Z2 of the test strip 9. The liquid L directly contacts only a bottom portion of the test strip 9, because the vent 42 limits the extent of liquid L able to enter the elongated hollow member 20. Liquid L does not directly wet the testing zones Z1,Z2. Thus, erroneous and unreliable test results caused by direct wetting of the zones Z1,Z2 by the liquid L are avoided.

While the vent 10 or 42 is shown as at least one hole in the elongated hollow member 2 or 20, the vent 10 or 42 could be defined by a mesh (not shown). The mesh may cover one or all of the vents 10 or 42. Alternatively, the mesh may constitute the entire bottom portion of the elongated hollow member 2 or 20 where the top edge of the mesh defines the extent that the liquid L enters the elongated hollow member 2 or 20.

Figure 9:
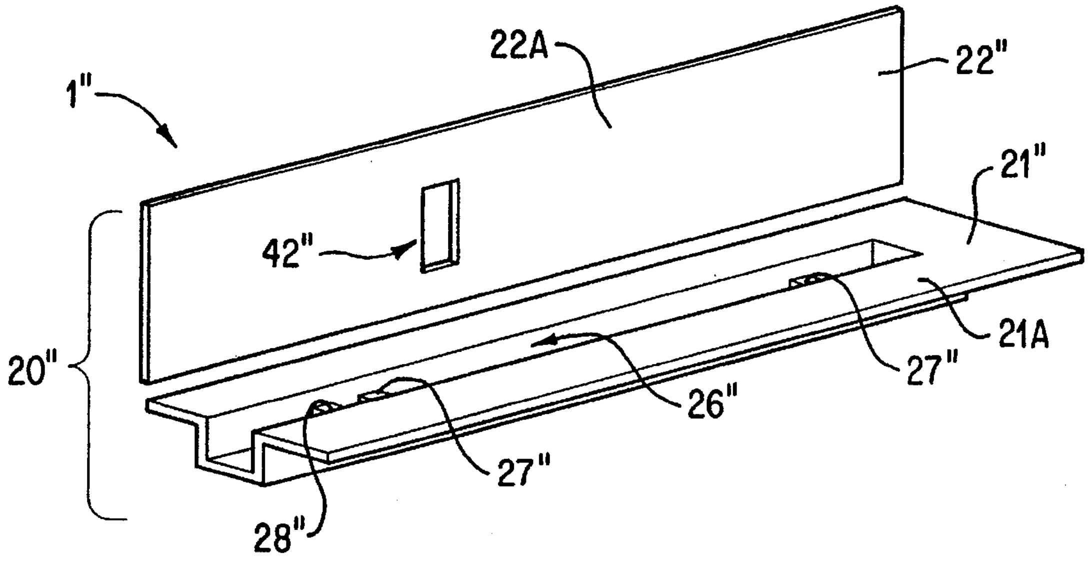
FIG. 9 is a front view of the test strip holder in the open condition according to a third embodiment of the invention.
Figure 10:
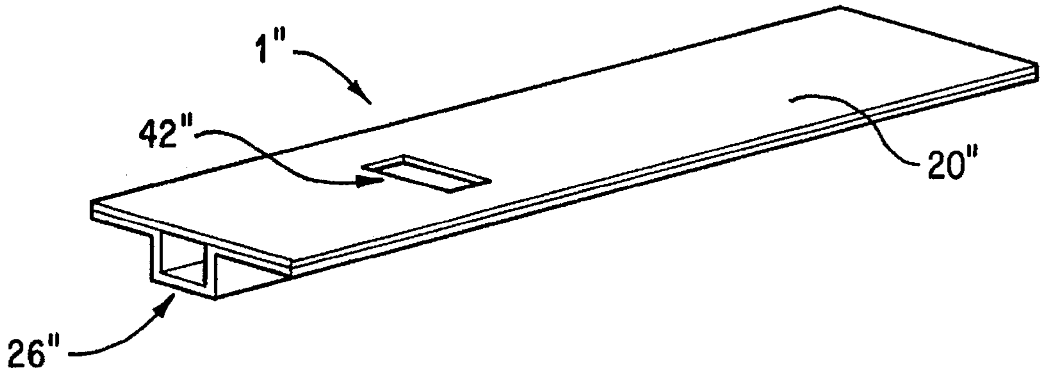
FIG. 10 is a front view of the test strip holder in a closed condition of FIG. 9.

FIGS. 9 and 10 illustrate a third embodiment of the test strip holder. The test strip holder 1" is similar in construction to the second embodiment and similar elements are designated with similar, but primed, reference characters.

The test strip holder 1" includes an elongated hollow member 20", which is formed from a test strip receiving part 21", which positions the test strip, and a test strip covering part 22". Unlike the second embodiment, the test strip receiving part 21" and the test strip covering part 22" are not hingedly connected and are separate components before being brought together to form the elongated hollow member 20".

In the embodiment of FIGS. 9 and 10, the test strip receiving part 21" includes a planar surface 21A, which is spaced from a test strip receiving channel 26". The test strip covering part 22" includes a mating planar surface 22A, which is formed in a shape and size complementary to the planar surface 21A. When the test strip covering part 22" is brought into overlying relation to the test strip receiving part 21", the planar surfaces 21A,22A mate together. The surfaces can then be sealingly joined together by an appropriate method of connection, such as sealing by ultrasonic welding, rf (radio frequency) welding, plasma welding, adhesive or the like.

The overall design of the test strip holder, including the vent, measures and permits only a specific volume of liquid to be presented to the test strip. The volume is a final volume of liquid in the test strip itself after the pads and membrane are saturated. This volume can be adjusted by changing the wicking capacity of the test strip components.

While this invention has been described in conjunction with specific embodiments thereof, it is evident that many alternatives, modifications and variations will be apparent to those skilled in the art. Accordingly, the preferred embodiments of the invention as set forth herein are intended to be illustrative. Various changes may be made without departing from the spirit and scope of the invention as defined in the following claims.

What is claimed is:

1. A test strip holding apparatus, comprising:

an elongated hollow member having an open end and a closed end;

a support configured to hold a test strip within the elongated hollow member in a position spaced from inner walls of the elongated hollow member; and at least one vent positioned between the open end and the closed end, said at least one vent being spaced from the open end and the closed end, wherein said at least one vent vents the elongated hollow member at a distance from the closed end and by air pressure in the closed end limits a maximum height that a liquid can travel through said elongated hollow member from said open end toward said closed end other than by capillary force along a test strip when said open end is dipped into said liquid.

2. The apparatus according to claim 1, wherein the at least one vent comprises a plurality of vents.

3. An apparatus according to claim 1, wherein the elongated hollow member has a circular cross-section.

4. An apparatus according to claim 1, wherein the closed end is formed by walls of the elongated hollow member.

5. An apparatus according to claim 1, wherein the closed end is closed by a sealing plug.

6. An apparatus according to claim 1, wherein the open end includes a plug having a through passage inserted into the open end of the elongated hollow member.

7. An apparatus according to claim 6, wherein the plug defines at least a portion of the support.

8. An apparatus according to claim 6, wherein the through passage has a diameter substantially equivalent to the width of the test strip to frictionally support the test strip within the through passage of the plug, spaced from inner walls of the elongated hollow member.

9. An apparatus according to claim 1, further including a test strip held by the support.

10. An apparatus according to claim 1, wherein the elongated hollow member includes a test strip receiving part and a test strip covering part, wherein the test strip receiving part is connectable to the test strip covering part.

11. An apparatus according to claim 10, wherein the elongated hollow member includes a test strip receiving part, including a flat surface and a test strip covering part including another flat surface complimentary with the flat surface, wherein the flat surface and the another flat surface are sealed together.

12. An apparatus according to claim 10, wherein one of the test strip covering part and the test strip receiving part includes a groove and the other of the test strip covering part and the test strip receiving part includes a projection, the projection being configured to sealingly fit into the groove, wherein the groove and projection fit together to define the elongated hollow member.

13. An apparatus according to claim 10, wherein the test strip receiving part includes a test strip channel configured to receive the test strip, the support being located within the test strip channel.

14. An apparatus according to claim 13, further including a stop proximate the open end capable of maintaining the test strip within the test strip channel.

15. An apparatus according to claim 13, wherein the channel comprises a center planar support surface surrounded by raised side portions that constrain movement of a test strip.

16. An apparatus according to claim 10, wherein the at least one vent is formed in the test strip covering part.

17. A method of testing a liquid using a test strip within a test strip holder, the method comprising the steps of:

supporting a test strip within an elongated hollow member having an open end, a closed end and a sidewall with at least one vent in the sidewall between and spaced from the open end and the closed end, the test strip being spaced from inner walls of the elongated hollow member;

immersing the elongated hollow member into a liquid to be tested to at least a depth of the at least one vent, wherein said at least one vent vents the elongated hollow member at a distance from the closed end and by air pressure in the closed end limits a maximum height that said liquid travels through said elongated hollow member from said open end toward said closed end other than by capillary force along said test strip when said open end is dipped into said liquid; and observing an effect of the liquid on the test strip above the at least one vent.

18. The method according to claim 17, wherein the step of supporting the test strip includes frictionally supporting the test strip at a portion of the hollow member where liquid enters.

19. The method according to claim 17, wherein the step of supporting the test strip includes supporting the test strip at a plurality of locations.

20. The method according to claim 17, wherein liquid travels up the test strip only by capillary action within the test strip.

21. A test strip holding apparatus, comprising:

means for supporting a test strip within and spaced from inner walls of means for receiving a test strip having an open end and a closed end;

means for venting the means for receiving between the open end and the closed end and at a distance from the closed end which by air pressure in the closed end limits a maximum height that a liquid can travel through said receiving means from said open end toward said closed end other than by capillary force along a test strip as the open end of the means for receiving is dipped into the liquid, said venting means being spaced from the open end and the closed end; and means for observing the effect of the liquid on the test strip.

22. The apparatus according to claim 21, wherein the means for observing comprises a window in the means for receiving.

23. An apparatus according to claim 21, further including a test strip held by the supporting means.

24. A method for testing a liquid, comprising:

supporting a test strip within and spaced from inner walls of means for receiving a test strip having an open end and a closed end;

venting the means for receiving through means for venting between the open end and the closed end and at a distance from the closed end to limit, by air pressure in the closed end, a maximum height that a liquid can travel through said receiving means from said open end toward said closed end other than by capillary force along a test strip as the open end of the means for receiving is dipped into the liquid, the means for venting being spaced from the open end and the closed end; and observing the effect of the liquid on the test strip.

* * * * *